US006605716B2

(12) United States Patent
Sorger et al.

(10) Patent No.: US 6,605,716 B2
(45) Date of Patent: Aug. 12, 2003

(54) PROCESS FOR THE PREPARATION OF HYDROXY AND AMINO COMPOUNDS

(75) Inventors: Klaus Sorger, München (DE); Hermann Petersen, Burghausen (DE)

(73) Assignee: Consortium fuer Elektrochemische Industries, GmbH, Munich (DE)

( * ) Notice: Subject to any disclaimer, the term of this patent is extended or adjusted under 35 U.S.C. 154(b) by 0 days.

(21) Appl. No.: 09/891,800

(22) Filed: Jun. 26, 2001

(65) Prior Publication Data

US 2002/0013501 A1 Jan. 31, 2002

(30) Foreign Application Priority Data

Jun. 29, 2000 (DE) .......................... 100 31 604

(51) Int. Cl.$^7$ .................. C07D 205/00; C07C 51/00; C07C 69/76; C07C 69/66
(52) U.S. Cl. ................... 540/200; 554/153; 560/60; 560/179
(58) Field of Search ............ 560/179, 60; 554/153; 540/200

(56) References Cited

U.S. PATENT DOCUMENTS 5,091,598 A * 2/1992 Cahiez et al.
5,294,731 A 3/1994 Paust et al.

FOREIGN PATENT DOCUMENTS

EP 562 343 9/1993

OTHER PUBLICATIONS

A. Fuerstner, "Recent Advancements in the Reformatsky Reactions," Synthesis, 1989, pp. 571–590.
Jacek K. Gawronski, "Tetrahedron Letters," vol. 25, No. 24, pp. 2605–2608, 1984.
E.W. Warnhoff, M.Y.H. Wong, P.S. Raman, Can. J. Chem., 1981, 59, pp. 688–696.
G. Picotin, P. Miginiac, J. Org. Chem., 1987, 52, pp. 4796–4798.
H. Gilman, M. Speeter, J. Am. Chem. Soc., 1943, 65, p. 2255.
A.K. Bose et al., J. Chem. Soc., Chem. Commun., 1984, p. 86.

* cited by examiner

Primary Examiner—Johann Richter
Assistant Examiner—Paul A. Zucker
(74) Attorney, Agent, or Firm—Brooks & Kushman P.C.

(57) ABSTRACT

A process for the preparation of hydroxy and amino compounds, in which, in a first step, an aldehyde, ketone or imine is reacted in a Reformatsky reaction with a reactive halogen compound and zinc, in carboxylic esters as solvents, the reactive halogen compound being brought into contact with the zinc at the same time as or after contact with the aldehyde, ketone or imine, and in a second step, the reaction product of the first step is hydrolyzed.

20 Claims, No Drawings

PROCESS FOR THE PREPARATION OF HYDROXY AND AMINO COMPOUNDS

BACKGROUND OF THE INVENTION

1. Field of the Invention

The invention relates to a process for the preparation of hydroxy and amino compounds.

2. Background Art

The reaction of reactive halogen compounds, in particular α-halocarbonyl compounds, with electrophilic substrates in the presence of zinc metal is known as Reformatsky reaction. Examples of electrophilic substrates include aldehydes, ketones, imines, nitriles, carboxylic anhydrides, carbonyl chlorides, lactones, orthoformates, formates, epoxides, azirines, aminals and nitrones. The reaction is important for the synthesis of building blocks for the preparation of pharmaceutical active ingredients, fragrances and crop protection compositions.

The choice of solvent, the method of activation of the zinc used, and in general the nature of overall reaction mixture, are of decisive importance for achieving good yields and high selectivities, and thus high product purity.

Particularly suitable solvents for the Reformatsky reaction are ethers such as diethyl ether, 1,4-dioxane, dimethoxymethane, dimethoxyethane and, in particular, tetrahydrofuran. In addition, other solvents which have proven effective are aromatic hydrocarbons or mixtures of the abovementioned ethers with aromatic hydrocarbons, mixtures of tetrahydrofuran and trimethyl borate, and the polar solvents acetonitrile, dimethylformamide, dimethylacetamide, dimethyl sulfoxide and hexamethylphosphoric triamide. A useful summary of the reaction may be found in A. Fürstner, SYNTHESIS 1989, p. 571. European published application EP-A-562 343 discloses that the reaction of α-bromocarboxylic esters with carbonyl compounds in the presence of zinc in methylene chloride solvent proceeds with high yields. However, the use of the foregoing solvents or solvent mixtures have numerous disadvantages.

The water-miscible ethers 1,4-dioxane and tetrahydrofuran, and the water-miscible polar solvents acetonitrile, dimethylformamide, dimethylacetamide, dimethyl sulfoxide and hexamethylphosphoric triamide, dissolve during aqueous hydrolysis of the zinc compounds and zinc salts formed in the aqueous phase. For economical reasons and to reduce the amounts of waste, particularly in industrial scale processes, recovery of the solvents from the aqueous phase, e.g. by extraction or distillation, is necessary. This recovery, however, is expensive, and adds considerable cost to the process.

In addition, in the case of the use of the abovementioned water-miscible solvents for the hydrolysis of the reaction mixture, it is usually necessary to use a water-immiscible organic solvent, such as ethyl acetate or methyl tert-butyl ether as cosolvents, to improve phase separation. These solvents must also be recovered and freed from impurities by distillation prior to reuse, again, an expensive process. If solvent mixtures are used for Reformatsky reactions, the recovery, separation and optional purification of the individual solvents used generally requires further expense.

Use of diethyl ether, 1,4-dioxane, dimethoxymethane, dimethoxyethane and tetrahydrofuran as solvents for Reformatsky reactions is further disadvantageous, as these ether solvents have a tendency, as a result of autoxidation, to form explosive peroxides. This tendency to produce peroxides makes the use of such solvents hazardous on an industrial scale. When recovery and repeated use is contemplated, their use is yet more difficult, or possible only with large expenditure, due to the danger of accumulation of explosive constituents.

The use of methylene chloride as a solvent as taught by EP-A-562 343, or the use of other halogenated hydrocarbons is unacceptable for reasons of environmental concerns, and should therefore be avoided, particularly on an industrial scale. In addition, many of the abovementioned solvents are expensive, which additionally adversely affects the economy of the reaction unless the solvent is recovered.

There was therefore still a need for a suitable solvent for the reaction of electrophilic substrates such as aldehydes, ketones and imines with reactive halogen compounds in the presence of zinc, which allows the reaction, particularly on an industrial scale, to be carried out in an environmentally responsible and cost-effective manner, without the use of solvent mixtures or the addition of cosolvents. Coupled with the use of such solvent should be the simplest possible recovery method for the solvent, thus allowing reduction in the amounts of waste. However, the solvent should not lower the yield and selectivity compared with previously known solvents.

SUMMARY OF THE INVENTION

The invention provides a process for the preparation of hydroxy and amino compounds, in which, in a first step, aldehydes, ketones or imine electrophiles are reacted in a Reformatsky reaction with a reactive halogen compound and zinc in carboxylic esters as solvents, the reactive halogen compound being brought into contact with the zinc at the same time as or after contact with the aldehydes, ketones or imines; and, in a second step, the reaction product of the first step is hydrolyzed.

DETAILED DESCRIPTION OF THE PREFERRED EMBODIMENT(S)

Preference is given to a process for the preparation of hydroxy and amino compounds of the general formula (1)

$$R^1R^2C(W^x)-R^3R^4C-(X)_a-Y \qquad (1)$$

comprising reacting, in a first step, aldehydes, ketones or imines of the general formula (2)

$$R^1R^2C=W \qquad (2)$$

with zinc and reactive halogen compounds of the general formula (3)

$$Hal-R^3R^4C-(X)_a-Y \qquad (3),$$

in a carboxylic ester solvent of the general formula (4)

$$R^5-((O(CH_2)_m)_n-COO-((CH_2)_o-COO)_p-((CH_2)_qO)_r-R^6 \qquad (4),$$

where $R^1$ and $R^2$ are hydrogen or an optionally halogen- or cyano-substituted $C_1$–$C_{30}$-hydrocarbon radical in which one or more nonadjacent methylene units can be replaced by —O—, —CO—, —COO—, —OCO—, or —OCOO—, —S— or —NR$^x$-groups and in which one more methine units can be replaced by —N= or —P= groups, $W^x$ is OH or $NHR^1$, W is O or $NR^1$, $R^3$ and $R^4$ are independently hydrogen, halogen or an optionally halogen-substituted $C_1$–$C_{30}$-hydrocarbon radical in which one or more nonadjacent methylene units can be replaced by —O—, —CO—, —COO—, —OCO—, or —OCOO—, —S— or —$NR^x$-groups and in which one more methine units can be replaced by —N= or —P= groups, X is chosen from

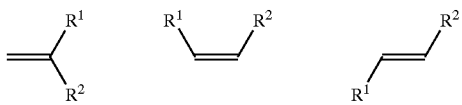

a is an integer with a value of 0 or 1,

Y is CN, (C=O)—Z, ($SO_2$)—Z, (P=O)(—Z)$_2$ or an aromatic radical, where one or more methine units in the ring can be replaced by —N= or —P= groups, and the ring can carry the hetero atoms —O—, —S— or —NH—, where the aromatic ring is optionally halogen- or cyano-substituted or substituted by $C_1$–$C_{30}$-hydrocarbon radicals in which one or more nonadjacent methylene units can be replaced by —O—, —CO—, —COO—, —OCO—, or —OCOO—, —S— or —$NR^x$-groups, Z is an optionally halogen-substituted $C_1$–$C_{30}$-hydrocarbon radical in which one or more nonadjacent methylene units can be replaced by —O—, —CO—, —COO—, —OCO—, or —OCOO—, —S—, or —$NR^x$-groups and in which one or more methine units can be replaced by —N= or —P= groups, OH, $OR^1$, $OSi(R^1)_3$, $NHR^1$ or $NR^1R^2$, Hal is chlorine, bromine or iodine, $R^5$ and $R^6$ are independently $C_1$–$C_{30}$-hydrocarbon radicals in which one or more nonadjacent methylene units can be replaced by —O— groups, $R^x$ is hydrogen or an optionally halogen-substituted $C_1$–$C_{30}$-hydrocarbon radical in which one or more nonadjacent methylene units can be replaced by —O—, —CO—, —COO—, —OCO—, or —OCOO—, —S—, —NH— or —$NCH_3$— groups and in which one or more methine units can be replaced by —N= or —P= groups, m, n, o, p, q and r are integers with a value of from 0 to 6, where in each case 2 radicals chosen from the pairs $R^1$ and $R^2$, $R^3$ and $R^4$, $R^1$ and $R^3$, $R^1$ and Y, $R^1$ and Z, $R^3$ and Y, $R^3$ and Z, $W^x$ and Y, and $W^x$ and Z, where $W^x$ is O— or $NR^1$- and Z can also be a direct bond, are linked together, where the reactive halogen compounds of the general formula (3) are brought into contact with the zinc at the same time as the compounds of the general formula (2) are brought into contact with zinc, or at a later time, and in a second step, hydrolyzing the reaction product of the first step.

Hydroxy and amino compounds of the general formula (1) can be prepared by the process according to the invention described above in very high yields, i.e. up to 90% or more, and at very high purities, in a simple manner and with very good space-time yields.

The process according to the invention has proven to be particularly simple on an industrial scale since the reaction can be carried out in commercially available carboxylic ester solvents of the general formula (4) without any pretreatment of these solvents, for example, distillation or drying, and neither the addition of a further solvent for carrying out the reaction or for the work-up, or a cosolvent for improved phase separation during work-up is required. Since no solvent mixtures are required, recovery of solvent has proven to be very straightforward. The preferred carboxylic esters of the general formula (4) have low solubility or dissolve only very slightly in water and can therefore be recovered easily and efficiently, for example during product isolation, making the reaction very economical. Thus, for example, ethyl acetate, isopropyl acetate or butyl acetate as solvents of the general formula (4) can be recovered during isolation of the prepared products by distillation, in very high yields.

As a result of the replacement of halogen-containing hydrocarbons and ether solvents sensitive to peroxide formation with carboxylic esters of the general formula (4), the process of the invention is not only more environmentally friendly, but is also associated with a significantly reduced hazard potential. In addition, the product yield and product quality of the hydroxy and amino compounds of the general formula (1) prepared by the process of the invention, are in many cases, improved as compared with previously known processes described in the literature. The use of carboxylic esters of the general formula (4) is, for the course of the reaction, for the product yields and purities, and for the elimination of secondary reactions, of particular advantage. In addition, in most cases it is possible to carry out the inventive process using a relatively low excess of zinc and reactive halogen compound of the general formula (3) based on the electrophilic reactants, the product yield and quality in many cases still being higher than when previously known solvents are used, which makes the process according to the invention yet more economical.

In the process according to the invention, preference is given to first introducing zinc and aldehyde, ketone or imine of the general formula (2) into the carboxylic ester of the general formula (4), and then adding the reactive halogen compound of the general formula (3), optionally dissolved in a solvent.

It is alternatively preferred to initially introduce zinc into the carboxylic ester of the general formula (4) and then to add a mixture of reactive halogen compound of the general formula (3) and aldehyde, ketone or imine of the general formula (2), optionally dissolved in a solvent.

From E. W. Warnhoff, M. Y. H. Wong, P. S. Raman, CAN. J. CHEM. 1981, 59, p. 688 it is known that α-halogenozinc carbonyl compounds (Reformatsky reagents) of the general formula (3), where Hal is halogenozinc, can react with carboxylic esters as electrophiles. It is believed that since aldehydes, ketones and imines are more electrophilic and thus more reactive than carboxylic acid derivatives such as the carboxylic ester solvents of the general formula (4), the former react preferably and more rapidly with halogenozinc carbonyl compounds of the general formula (3) (Reformatsky reagents) than the carboxylic ester solvents.

If zinc is first introduced into the carboxylic ester of the general formula (4), following which the reactive halogen compound of the general formula (3) is added and finally the electrophile is added, then the reaction would be expected to proceed with the formation of undesired by-products. For this reason, carboxylic esters of the general formula (4) have hitherto not been used as solvents for the reaction of aldehydes, ketones and imines with reactive halogen compounds and zinc or for the production of halogenozinc carbonyl compounds of the general formula (3) (Reformatsky reagents), where Hal is halogenozinc.

The $C_1$–$C_{30}$-hydrocarbon radicals for $R^1$, $R^2$, $R^3$, $R^4$ and Z are preferably linear, branched or cyclic $C_1$–$C_{20}$-alkyl, $C_2$–$C_{20}$-alkenyl, $C_5$–$C_{20}$-acetalalkenyl, or $C_3$–$C_{20}$-alkoxycarbonylalkyl radicals, optionally substituted by F, Cl, Br, I, CN and $C_1$–$C_8$-alkoxy radicals; aryl, aralkyl, alkaryl, aralkenyl, alkenylaryl radicals in which one or more methine units may be replaced by —N= or —P= groups and methylene units may be replaced by —O—, —S—, —NH—, and optionally substituted by F, Cl, Br, I, CN and $C_1$–$C_{10}$-alkoxy radicals, and which optionally carry $C_1$–$C_{10}$-alkyl radicals on the ring and optionally hetero atoms —O—, —S— or —NH— in the ring.

The radicals $R^1$ and $R^2$, $R^3$ and $R^4$, $R^1$ and $R^3$, $R^1$ and Y, $R^1$ and Z, $R^3$ and Y, $R^3$ and Z, $W^x$ and Y and $W^x$ and Z, where $W^x$ is O—or $NR^1$- and Z can also be a direct bond, or can be linked together to form a variety of ring structures when such linkages are possible. The radicals $R^1$ and $R^3$, $R^1$ and Y, $R^1$ and Z, $W^x$ and Y, and $W^x$ and Z, where $W^x$ is O— or $NR^1$- and Z can be a direct bond, can, for example, be linked together by intramolecular reaction.

When $R^3$ and $R^4$ are halogen radicals, they are preferably F and Cl. In particular, a has the value 0.

As reactive halogen compounds of the general formula (3), preference is given to using bromine compounds, where Hal in the general formula (3) is bromine. Preference is given to reactive halogen compounds of the general formula (3) in which Y is (C=O)—Z. Also preferred are reactive halogen compounds of the general formula (3) in which Z is $OR^1$. Particularly preferred reactive halogen compounds of the general formula (3) are α-bromocarboxylic esters.

Zinc is preferably used in the form of films, ribbon, pieces, powder, or dust form, or in the form of zinc wool. The presence of other metals such as copper, silver or mercury is not required. Most preferably, zinc is used in the form of commercially available, standard commercial zinc powder or zinc dust.

To achieve higher product yields, it has proven useful to activate the zinc prior to the addition of the aldehyde, ketone or imine of the general formula (2) and the reactive halogen compound of the general formula (3) or mixture thereof. For zinc activation, previously known methods which are customarily used and are given, for example, in the summary by A. Fürstner, SYNTHESIS 1989, p. 571, are suitable. Methods which have proven quite successful are washing of the zinc with acid, activation by iodine, as described in EP-A-562 343, and activation by trimethylchlorosilane, the activation by trimethylchlorosilane being particularly preferred because it is simple to carry out and because of increased yields, product purities and selectivities, and suppression of secondary reactions. The activation of zinc by trimethylchlorosilane in the diethyl ether solvent is known from G. Picotin, P. Miginiac, J. ORG. CHEM. 1987, 52, p. 4796.

For activation of zinc with trimethylchlorosilane, zinc is introduced into the carboxylic ester of the general formula (4), then trimethylchlorosilane is added and the mixture is heated for 10 min to 2 h, preferably 10 to 45 min, at temperatures of from 30 to 150° C., preferably at 40 to 120° C., and more preferably at 50 to 90° C. It has proven successful to react the zinc with trimethylchlorosilane in the carboxylic ester of the general formula (5) in a molar ratio of 1:(0.01 to 0.5), in particular 1:(0.05 to 0.3) accompanied by heating to the desired temperature.

In the carboxylic esters of the general formula (4), $R^5$ and $R^6$ are preferably straight-chain, branched or cyclic $C_1$–$C_{10}$-alkyl, $C_6$–$C_{10}$-aralkyl, $C_2$–$C_{10}$-alkoxyalkyl radicals or $C_5$–$C_{10}$-aryl radicals. In particular, $R^5$ and $R^6$ are straight-chain or branched $C_1$–$C_8$-alkyl radicals. The subscripts m, n, o, p, q and r are preferably integers with a value of 0, 1, 2 or 3. In particular, n, p and r are 0.

Particularly preferred carboxylic esters of the general formula (4) are methyl, ethyl, n-propyl, i-propyl, n-butyl, i-butyl, t-butyl, n-hexyl, n-pentyl, and i-pentyl esters of acetic acid, propionic acid and butyric acid and mixed $C_{6-14}$ alkyl acetates. The esters and the acetic alkyl acetate mixtures can be recovered in very high yield during isolation of the products, and subsequently reused. If the cost-effective methyl acetate is used as solvent of the general formula (4), it is possible to dispense with a recovery step.

For the activation of the reaction mixture, it is also possible to use additives such as compounds of copper, chromium, manganese, cobalt, bismuth, samarium, scandium, indium, titanium, cerium, tellurium, tin, lead, antimony, germanium, aluminum, magnesium, palladium, nickel and mercury, or, where appropriate, mixtures thereof.

During the reaction in the first step, the temperature of the exothermic reaction is preferably maintained at a designated value, where necessary by cooling. The upper temperature limit may be regulated by the boiling point of the solvent of the general formula (4) used, such as, for example ethyl acetate (b.p.: 77° C.) or isopropyl acetate (b.p.: 87–89° C.). In the case of higher-boiling solvents of the general formula (4), such as, for example, n-butyl acetate (b.p.: 124–126° C.), the temperature of the reaction is preferably controlled by cooling. The reaction is preferably carried out at temperatures of from −20 to 150° C., more preferably at 20 to 110° C., and in particular at 40 to 90° C.

The pressure range of the reaction is not critical and can be varied within wide limits. The pressure is usually 0.01 to 20 bar, and preference is given to carrying out the reaction under atmospheric pressure. The reaction is preferably performed without blanketing with protective gas such as nitrogen or argon, although such blanketing can be performed if desired. The reaction can be carried out continuously or batchwise, preferably batchwise.

When the addition of all participating constituents is complete, the reaction is preferably "post-reacted" for a further 5 min to 3 h, more preferably 5 min to 1.5 h, and in particular 5 to 30 min, in order to complete the reaction. Excess zinc metal can be separated off by filtration. It is also possible to dissolve excess zinc in the acid used in the second step for the hydrolysis of the reaction mixture.

It has proven successful to react the zinc with the reactive halogen compound of the general formula (3) and the electrophile of the general formula (2) in the molar ratio (1 to 3):(1 to 2):1, in particular (1.1 to 1.7):(1 to 1.3):1.

The process according to the invention has proven advantageous compared with previously known processes, since in most cases the post-reaction time of 5 to 30 min is considerably shortened. As a result, particularly on an industrial scale, very good space-time yields and thus high efficiency is obtained. Very short post-reaction times arise, in particular, following activation of the reaction mixture or of the zinc by trialkylchlorosilane in the carboxylic ester solvent.

After the reaction in the first step has taken place, the reaction mixture is hydrolyzed in the second step, generally at temperatures of from −30 to 60° C., more preferably from −10 to 30° C., by the addition of an aqueous acid or base, as a result of which zinc compounds and zinc salts dissolve. Alternatively, the reaction mixture can be added to an aqueous acid or base. Preferred bases are ammonia and organic amines such as trialkylamines and alkanolamines.

Preferred acids are Brönstedt acids, in particular strong acids, such as boric acid, tetrafluoroboric acid, nitric acid, nitrous acid, phosphoric acid, phosphorous acid, hypophosphorous acid, sulfuric acid, sulfurous acid, peroxysulfuric acid, hydrochloric acid, hydrofluoric acid, hydroiodic acid, hydrobromic acid, perchloric acid, hexafluorophosphoric acid, benzenesulfonic acid, p-toluenesulfonic acid, methanesulfonic acid, and trifluoromethanesulfonic acid; and carboxylic acids such as chloroacetic acid, trichloroacetic acid, acetic acid, acrylic acid, benzoic acid, trifluoroacetic acid, citric acid, crotonic acid, formic acid, fumaric acid, maleic acid, malonic acid, gallic acid, itaconic acid, lactic acid, tartaric acid, oxalic acid, phthalic acid and succinic acid.

In particular, ammonia, hydrochloric acid, sulfuric acid or citric acid, preferably ammonia, hydrochloric acid or citric acid, are used. The acid or base may be used in concentrated form or in the form of a dilute aqueous solution.

The products of the general formula (1) can be isolated by known, customarily used methods, such as extraction, distillation, crystallization, or by means of chromatographic methods. In most cases, the crude product obtained following removal of the solvent is of very high purity or of adequate purity and can be used directly in subsequent reactions and conversions, in particular ester hydrolyses.

All of the above symbols in the formulae above have their meanings independently of one another. The term "a" means "one or more" unless indicated otherwise. In the examples below, unless stated otherwise, all amounts and percentages are based on the weight, all pressures are 0.10 MPa (abs.) and all temperatures are 20° C.

EXAMPLE 1

Preparation of Ethyl 3-hydroxy-3-methylcaproate

At room temperature, a three-necked flask fitted with reflux condenser, internal thermometer, dropping funnel and stirrer was charged, under nitrogen protective gas, with 11.2 g of zinc powder (170 mmol) in 65 ml of isopropyl acetate. After 3.2 ml of trimethylchlorosilane (25 mmol) had been added, the mixture was heated at 65° C. for 30 min, then left to cool to 60° C., following which 9.7 g of neat pentan-2-one (113 mmol) were added and then, over the course of 8 min, 22.6 g of neat ethyl bromoacetate (136 mmol) were added dropwise, the temperature being maintained at 60° C. by external cooling. The mixture was then stirred for 25 min at 60° C., and following cooling to 0° C., was acidified with 65 ml of 2 N hydrochloric acid to a pH of 1 and stirred for 30 min. Excess zinc was removed by filtration, and the organic phase separated. The organic phase was stirred at 0° C. with 60 ml of 1 N hydrochloric acid and then washed with 30 ml of saturated sodium hydrogen carbonate solution. Following phase separation and drying over sodium sulfate, the solvent was removed by distillation under reduced pressure. The isopropyl acetate solvent was recovered to an extent of greater than 90%). Distillation gave ethyl 3-hydroxy-3-methylcaproate in a yield of 18.2 g (93% of theory) with a boiling point of 41° C. (0.31 mbar).

Analogous preparations in the solvents ethyl acetate, n-butyl acetate and methyl acetate produced ethyl 3-hydroxy-3-methylcaproate in yields of 17.2 g, 16.7 g and 16.2 g (88, 85 and 83% of theory, respectively).

EXAMPLE 2

Preparation of Methyl 3-hydroxy-3-phenyl-4-trifluorobutyrate

At room temperature, a three-necked flask fitted with reflux condenser, internal thermometer, dropping funnel and stirrer was charged, under nitrogen protective gas, with 5.7 g of zinc powder (86 mmol) in 35 ml of ethyl acetate. After 1.63 ml of trimethylchlorosilane (12.8 mmol) had been added, the mixture was heated at 65° C for 30 min, then left to cool to 60° C., following which, over the course of 10 min, a mixture of 10.6 g of methyl bromoacetate (69 mmol) and 10 g of ω,ω,ω-trifluoroacetophenone (58 mmol) was added dropwise, the temperature being maintained at 65° C. by external cooling. The mixture was then stirred for 30 min at 60° C., and following cooling to 0° C., was acidified with 35 ml of 2 N hydrochloric acid to a pH of 1 and stirred for 30 min. Excess zinc was removed by filtration, and the organic phase separated. The organic phase was then stirred at 0° C. with 30 ml of 0.5 N hydrochloric acid and finally washed with 20 ml of saturated sodium hydrogen carbonate solution. Following phase separation and drying over sodium sulfate, the solvent was removed by distillation under reduced pressure. Methyl 3-hydroxy-3-phenyl-4-trifluorobutyrate was obtained in a yield of 13.5 g (94% of theory). The compound has a melting point of 55° C. after recrystallization from petroleum ether.

EXAMPLE 3

Preparation of Methyl 3-hydroxy-2-methyl-3-phenylbutyrate

At room temperature, a three-necked flask fitted with reflux condenser, internal thermometer, dropping funnel and stirrer was charged, under nitrogen protective gas, with 8.6 g of zinc powder (130 mmol) in 53 ml of ethyl acetate. After 2.5 ml of trimethylchlorosilane (19.5 mmol) had been added, the mixture was heated at 65° C. for 30 min, then left to cool to 60° C., following which 10.5 g of acetophenone (87 mmol) were added, and over the course of 6 min, 17.4 g of methyl 2-bromopropionate (104 mmol) were then added dropwise, the temperature being maintained at 65° C. by external cooling. The mixture was stirred at 60° C. for 25 min, and following cooling to 0° C., acidified with 70 ml of 2 N hydrochloric acid to a pH of 1 and stirred for 30 min. Excess zinc was removed by filtration and the organic phase separated. The organic phase was then stirred at 0° C. with 70 ml of 0.5 N hydrochloric acid and finally washed with 30 ml of saturated sodium hydrogen carbonate solution. Following phase separation and drying over sodium sulfate, the solvent was removed by distillation under reduced pressure. Methyl 3-hydroxy-2-methyl-3-phenylbutyrate was obtained in a yield of 15.5 g (91% of theory) with a boiling point of 64° C. (0.03 mbar). The diastereomer ratio of the product was 2:1.

EXAMPLE 4

Preparation of methyl 3-hydroxy-3-(2'-phenylethenyl)caproate

At room temperature, a three-necked flask fitted with reflux condenser, internal thermometer, dropping funnel and stirrer was charged, under nitrogen protective gas, with 8.5 g of zinc powder (129 mmol) in 55 ml of ethyl acetate. After 2.4 ml of trimethylchlorosilane (19 mmol) had been added, the mixture was heated at 65° C. for 30 min, then left to cool to 50° C. Over the course of 8 min, a mixture of 15 g of 1-phenylhex-1-en-3-one, prepared by base-catalyzed aldol condensation of benzaldehyde and pentan-2-one, and 15.8 g of methyl bromoacetate (103 mmol) was added dropwise, the temperature being maintained at 50° C. by external cooling. The mixture was then stirred at 50° C. for 30 min, and following cooling to 0° C., acidified with 60 ml of 2 N hydrochloric acid to a pH of 1 and stirred for 30 min. Excess zinc was then removed by filtration and the organic phase separated. The organic phase was then stirred at 0° C. with 60 ml of 0.5 N hydrochloric acid and finally washed with 20 ml of saturated sodium hydrogen carbonate solution. Following phase separation and drying over sodium sulfate, the solvent was removed by distillation under reduced pressure. Methyl 3-hydroxy-3-(2'-phenylethenyl)caproate was obtained in a yield of 20.4 g (95% of theory) and a purity of greater than 97% (HPLC). The compound had a melting point of 43° C. following recrystallization from petroleum ether.

EXAMPLE 5

Preparation of Methyl 3-hydroxy-3-(2'-phenylethyl) caproate

At room temperature, a three-necked flask fitted with reflux condenser, internal thermometer, dropping funnel and stirrer was charged, under nitrogen protective gas, with 5.6 g of zinc powder (85 mmol) in 35 ml of ethyl acetate. After 1.61 ml of trimethylchlorosilane (12.6 mmol) had been added, the mixture was heated at 65° C. for 30 min, then left to cool to 60° C., following which 10 g of neat 1-phenylhexan-3-one prepared by base-catalyzed aldol condensation of benzaldehyde and pentan-2-one and subsequent hydrogenation of the resulting 1-phenylhex-1-en-3-one were added. Subsequently, over the course of 5 min, 10.4 g of methyl bromoacetate (68 mmol) were added dropwise, the temperature being maintained at 65° C. by external cooling. The mixture was stirred for 30 min at 60° C., and following cooling to 0° C., acidified with 35 ml of 2 N hydrochloric acid to a pH of 1 and stirred for 30 min. Excess zinc was removed by filtration and the organic phase separated. The organic phase was then stirred at 0° C. with 30 ml of 0.5 N hydrochloric acid and finally washed with 20 ml of saturated sodium hydrogen carbonate solution. Following phase separation and drying over sodium sulfate, the solvent was removed by distillation under reduced pressure. Methyl 3-hydroxy-3-(2'-phenylethyl)caproate was obtained in a yield of 13.5 g (95% of theory) and a purity of greater than 97% (HPLC).

EXAMPLE 6

Preparation of Methyl 3-hydroxy-3-phenylpropionate

At room temperature, a three-necked flask fitted with reflux condenser, internal thermometer, dropping funnel and stirrer was charged, under nitrogen protective gas, with 5.7 g of zinc powder (87 mmol) in 35 ml of isopropyl acetate. After 1.65 ml of trimethylchlorosilane (13 mmol) had been added, the mixture was heated at 65° C. for 30 min. Following cooling to 60° C., 6.2 g of benzaldehyde (58 mmol) were added and, over the course of 4 min, 10.6 g of methyl bromoacetate (70 mmol) were added dropwise at 55° C., the temperature being maintained at 55° C. by external cooling. The mixture was then stirred at 55° C. for 5 min and, after cooling to 0° C., acidified with 40 ml of 2 N hydrochloric acid to a pH of 1 and stirred for 30 min. Excess zinc was removed by filtration and the organic phase separated. The organic phase was then stirred at 0° C. with 40 ml of 0.5 N hydrochloric acid and finally washed with 20 ml of saturated sodium hydrogen carbonate solution. Following phase separation and drying over sodium sulfate, the solvent was distilled off under reduced pressure. Methyl 3-hydroxy-3-phenylpropionate was obtained in a yield of 8.9 g (85% of theory) with a boiling point of 76° C. (0.07 mbar).

An analogous preparation in the solvent ethyl acetate produced methyl 3-hydroxy-3-phenylpropionate in a yield of 9.1 g (87% of theory).

EXAMPLE 7

Preparation of 3-hydroxydecanoic Acid

At room temperature, a three-necked flask fitted with reflux condenser, internal thermometer, dropping funnel and stirrer was charged, under nitrogen protective gas, with 11.1 g of zinc powder (169 mmol) in 70 ml of ethyl acetate. After 3.2 ml of trimethylchlorosilane (25 mmol) had been added, the mixture was heated at 65° C. for 30 min, then left to cool to 60° C., following which, over the course of 6 min, a mixture of 21 g of methyl bromoacetate (137 mmol) and 16 g of octanal (125 mmol) was added dropwise, the temperature being maintained at 65° C. by external cooling. The mixture was then stirred at 55° C. for 5 min, and after cooling to 0° C., was acidified with 75 ml of 2 N hydrochloric acid to a pH of 1 and stirred for 30 min. Excess zinc was removed by filtration and the organic phase separated. The organic phase was then stirred at 0° C. with 80 ml of 1 N hydrochloric acid, and finally washed with 80 ml of saturated sodium hydrogen carbonate solution. Following phase separation, the solvent was removed by distillation under reduced pressure. For the ester hydrolysis, the crude product was treated with a solution of 15.4 g of potassium hydroxide (232 mmol) in 140 ml of water and stirred for 40 min at 50° C., during which a clear solution formed. The solution was extracted with 2×20 ml of toluene, and the aqueous phase was acidified at 0° C. with 100 ml of 2 N hydrochloric acid to a pH of 1 and extracted with 3×20 ml of ethyl acetate. The organic extracts were dried over sodium sulfate and the solvent was removed by distillation under reduced pressure. 3-Hydroxydecanoic acid was obtained in a yield of 21 g (89% of theory). The compound has a melting point of 58° C. following recrystallization from petroleum ether.

EXAMPLE 8

Preparation of Methyl 3-hydroxy-2-methyldecanoate

At room temperature, a three-necked flask fitted with reflux condenser, internal thermometer, dropping funnel and stirrer was charged, under nitrogen protective gas, with 5.5 g of zinc powder (84 mmol) in 34 ml of ethyl acetate. After 1.6 ml of trimethylchlorosilane (12.5 mmol) had been added, the mixture was heated at 65° C. Following cooling to 60° C., 7.2 g of octanal (56 mmol) were added, and over the course of 4 min, 11.2 g of methyl 2-bromopropionate (67 mmol) were added dropwise, the temperature being maintained at 65° C. by external cooling. The mixture was then stirred at 60° C. for 5 min and, after cooling to 0° C., acidified with 40 ml of 2 N hydrochloric acid to a pH of 1 and stirred for 30 min. Excess zinc was removed by filtration and the organic phase separated. The organic phase was then stirred at 0° C. with 40 ml of 0.5 N hydrochloric acid and finally washed with 20 ml of saturated sodium hydrogen carbonate solution. Following phase separation and drying over sodium sulfate, the solvent was removed by distillation under reduced pressure. Methyl 3-hydroxy-2-methyldecanoate was obtained in a yield of 10.2 g (85% of theory) with a boiling point of 68° C. (0.04 mbar). The diastereomer ratio was 2:1.

EXAMPLE 9

Preparation of N-phenyl-3-phenylacetidin-2-one

At room temperature, a three-necked flask fitted with reflux condenser, internal thermometer, dropping funnel and stirrer was charged, under nitrogen protective gas, with 7.6 g of zinc powder (115 mmol) in 45 ml of ethyl acetate. After 1.8 ml of trimethylchlorosilane (14 mmol) had been added, the mixture was heated at 70° C. for 30 min and then, over the course of 8 min, a mixture of 16.1 g of benzalaniline (89 mmol) and 16.3 g of methyl bromoacetate (100 mmol) was metered in, the temperature being maintained at 75° C. by external cooling. The mixture was then stirred at 60° C. for 30 min, and following cooling to 10° C., first treated with 130 ml of ethyl acetate, and then hydrolyzed with 80 ml of 25% strength ammonia solution. The mixture was then stirred at 55° C. for 20 min. Excess zinc was removed by filtration at elevated temperature and the organic phase separated. The organic phase was then washed at elevated temperature with 20 ml of water. Following phase separation, the solvent was removed by distillation under reduced pressure, yielding a crude product which consisted of 91.7 mol % of N-phenyl-3-phenylacetidin-2-one (β-lactam) and 8.3 mol % of methyl 3-(N-phenylamino)-3-phenylpropionate (β-amino acid ester), in a yield of 19.4 g (97% of theory) and a purity of greater than 95% (HPLC). Recrystallization from ethyl acetate gave N-phenyl-3-phenylacetidin-2-one with a melting point of 156° C. Following recrystallization from methanol, the melting point is 153–154° C.: H. Gilman, M. Speeter, J. AM. CHEM. Soc. 1943, 65, p. 2255).

According to A. K. Bose, K. Gupta and M. S., J. CHEM. SOC., Chem. Commun. 1984, p. 86, the preparation of N-phenyl-3-phenylacetidin-2-one takes place in a yield of 70% of theory.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention. It is understood that more than one aldehyde, ketone, and/or imine may take part in the reaction, although this is generally not desired. Likewise, more than one reactive halogen compound may be used. Again, this is not desired. The reaction preferably takes place in the absence of non-carboxylic ester solvents.

What is claimed is:

1. A process for the preparation of hydroxy and amino compounds, by means of a Reformatsky reaction, comprising:
    a) reacting an aldehyde, ketone, or imine with an organic halogen compound reactive in a Reformatsky reaction, and zinc metal in carboxylic ester solvent; and
    b) hydrolyzing the reaction product of the first step,
wherein said reactive halogen compound is contacted with zinc metal at the same time as with the aldehyde, ketone, or imine, or after the aldehyde, ketone or imine is contacted with zinc metal.

2. The process of claim 1, wherein hydroxy and amino compounds of the general formula (1)

are prepared by:
    a) reacting an aldehyde, ketone or imine of the general formula (2)

with zinc and a reactive halogen compound of the general formula (3)

in carboxylic ester solvent of the general formula (4)

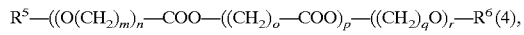

where
R$^1$ and R$^2$ are hydrogen or an optionally halogen- or cyano-substituted C$_1$–C$_{30}$-hydrocarbon radical in which one or more nonadjacent methylene units can be replaced by —O—, —CO—, —COO—, —OCO—, or —OCOO—, —S— or —NR$^x$— groups and in which one more methine units can be replaced by —N= or —P= groups, W$^x$ is OH or NHR$^1$, W is O or NR$^1$, R$^3$ and R$^4$ are independently hydrogen, halogen or an optionally halogen-substituted C$_1$–C$_{30}$-hydrocarbon radical in which one or more nonadjacent methylene units are optionally replaced by —O—, —CO—, —COO—, —OCO—, or —OCOO—, —S— or —NR$^x$— groups and in which one more methine units are optionally replaced by —N= or —P= groups, X is a divalent radical selected from the group consisting of

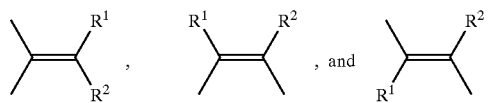

a is an integer with a value of 0 or 1,

Y is CN, (C=O)—Z, (SO$_2$)—Z, (P=O)(—Z)$_2$ or an aromatic radical, where one or more methine units in the ring of the aromatic radical are optionally replaced by —N= or —P= groups, and the ring can carry the hetero atoms —O—, —S— or —NH—, where the aromatic ring is optionally halogen- or cyano-substituted or substituted by C$_1$–C$_{30}$-hydrocarbon radicals in which one or more nonadjacent methylene units can be replaced by —O—, —CO—, —COO—, —OCO—, or —OCOO—, —S— or —NR$^x$— groups, Z is a direct bond or an optionally halogen-substituted C$_1$–C$_{30}$-hydrocarbon radical in which one or more nonadjacent methylene units are optionally replaced by —O—, —CO—, —COO—, —OCO—, or —OCOO—, —S—, or —NR$^x$— groups and in which one or more methine units are optionally replaced by —N= or —P= groups, OH, OR$^1$, OSi(R$^1$)$_3$, NHR$^1$ or NR$^1$R$^2$, Hal is chlorine, bromine or iodine, R$^5$ and R$^6$ are independently a C$_1$–C$_{30}$-hydrocarbon radical in which one or more nonadjacent methylene units can be replaced by —O— groups, R$^x$ is hydrogen or an optionally halogen-substituted C$_1$–C$_{30}$-hydrocarbon radical in which one or more nonadjacent methylene units can be replaced by —O—, —CO—, —COO—, —OCO—, or —OCOO—, —S—, —NH— or —NCH$_3$— groups and in which one or more methine units can be replaced by —N= or —P= groups, m, n, o, p, q and r are integers from 0 to 6, where in each case, pairs of radicals selected from the group consisting of the pairs $R^1$ and $R^2$, $R^3$ and $R^4$, $R^1$ and $R^3$, $R^1$ and Y, $R^1$ and Z, $R^3$ and Y, $R^3$ and Z, $W^x$ and Y, and $W^x$ and Z, where $W^x$ is O— or $NR^1$— are optionally linked together to form a cyclic structure.

3. The process of claim 1, wherein the reactive halogen compounds are bromine compounds.

4. The process of claim 2, wherein the reactive halogen compounds are bromine compounds.

5. The process of claim 2, wherein in the reactive halogen compounds of the general formula (3), Y is (C=O)—Z.

6. The process of claim 4, wherein in the reactive halogen compounds of the general formula (3), Y is (C=O)—Z.

7. The process of claim 5, wherein Z is $OR^1$.

8. The process of claim 1, wherein the reactive halogen compounds are α-bromocarboxylic esters.

9. The process of claim 2, wherein the reactive halogen compounds are α-bromocarboxylic esters.

10. The process of claim 3, wherein the reactive halogen compounds are α-bromocarboxylic esters.

11. The process of claim 4, wherein the reactive halogen compounds are α-bromocarboxylic esters.

12. The process of claim 5, wherein the reactive halogen compounds are α-bromocarboxylic esters.

13. The process of claim 7, wherein the reactive halogen compounds are α-bromocarboxylic esters.

14. The process of claim 1, wherein the carboxylic ester solvent(s) is selected from methyl, ethyl, n-propyl, i-propyl, n-butyl, i-butyl, t-butyl, n-hexyl, n-pentyl, i-pentyl acetates, propionates or butyrates, ($C_6$–$C_{14}$)-alkyl acetate mixtures, or mixtures of these solvents.

15. The process of claim 2, wherein the carboxylic ester solvent(s) is selected from methyl, ethyl, n-propyl, i-propyl, n-butyl, i-butyl, t-butyl, n-hexyl, n-pentyl, i-pentyl acetates, propionates or butyrates, ($C_6$–$C_{14}$)-alkyl acetate mixtures, or mixtures of these solvents.

16. The process of claim 1, wherein zinc metal is activated with trimethylchlorosilane.

17. The process of claim 2, wherein zinc metal is activated with trimethylchlorosilane.

18. The process of claim 3, wherein zinc metal is activated with trimethylchlorosilane.

19. The process of claim 5, wherein zinc metal is activated with trimethylchlorosilane.

20. The process of claim 16, wherein the zinc metal is activated with trimethylchlorosilane in a solvent consisting of one or more carboxylic esters.

* * * * *